US008617865B2

(12) United States Patent
Nakagawa et al.

(10) Patent No.: US 8,617,865 B2
(45) Date of Patent: Dec. 31, 2013

(54) TANNASE, GENE ENCODING SAME, AND PROCESS FOR PRODUCING SAME

(75) Inventors: Megumi Nakagawa, Kakamigahara (JP); Naoki Matsumoto, Kakamigahara (JP); Hitoshi Amano, Kakamigahara (JP); Shotaro Yamaguchi, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 240 days.

(21) Appl. No.: 13/124,510

(22) PCT Filed: Oct. 2, 2009

(86) PCT No.: PCT/JP2009/005105
§ 371 (c)(1),
(2), (4) Date: Apr. 15, 2011

(87) PCT Pub. No.: WO2010/047047
PCT Pub. Date: Apr. 29, 2010

(65) Prior Publication Data
US 2011/0195155 A1   Aug. 11, 2011

(30) Foreign Application Priority Data

Oct. 24, 2008   (JP) .................................. 2008-274360

(51) Int. Cl.
*C12N 9/14*   (2006.01)
(52) U.S. Cl.
USPC ............................ 435/195; 435/183; 435/194
(58) Field of Classification Search
USPC ......................................... 435/183, 194, 195
See application file for complete search history.

(56) References Cited

U.S. PATENT DOCUMENTS

| 2003/0082595 A1 | 5/2003 | Jiang et al. |
| 2004/0082053 A1 | 4/2004 | Machida et al. |

FOREIGN PATENT DOCUMENTS

| CN | 101260392 A | 9/2008 |
| JP | 48-035478 B2 | 10/1973 |
| JP | 08-080196 A | 3/1996 |
| JP | 2003-250588 A | 9/2003 |
| WO | WO-03/012071 A2 | 2/2003 |

OTHER PUBLICATIONS

Barthomeuf et al. [Journal of Fermentation & Bioengineering (1994), 77(3): 320-232].*
Kanauchi et al. [Journal of Food Science (Aug. 2008): 73(6): C458-C463].*
Accession No. A1DD15 (Jan. 23, 2007).*
Banerjee et al., "Production and characterization of extracellular and intracellular tannase from newly isolated *Aspergillus aculeatus* DBF 9." *Journal of Basic Microbiology*, vol. 41, Issue 6, pp. 313-318, Dec. 2001.
An extended European Search Report issued in corresponding European Patent Application No. 09821747.4, dated Jul. 5, 2012.
Cristóbal N. Aguilar et al., "Microbial tannases: advances and perspectives," Appl. Microbiol. Biotechnol., vol. 76, 2007, pp. 47-59.
Osamu Hatamoto et al., "Cloning and sequencing of the gene encoding tannase and a structural study of the tannase subunit from *Aspergillus oryzae*," Gene, vol. 175, 1996, pp. 215-221.
Food Safety Commission, "Safety evaluation standard of additives produced in use of genetically modified organisms" determined on Mar. 25, 2004, pp. 1-10.
M. Ascención et al., "A novel tannase from *Aspergillus niger* with β-glucosidase activity," Microbiology, vol. 149, 2003, pp. 2941-2946.
Batra, A. et al., "Potential tannase producers from the genera *Aspergillus* and *Penicillium*," Process Biochemistry, vol. 40, 2005, pp. 1553-1557.
Robert, W-J., "Tannase from *Aspergillus awamori*: Purification, characterization, and the elucidation of the role of tannins in lowering in vitro protein digestibility of black beans," Dissertation Abstract. International B, vol. 50, Bo.7, 1989, p. 2902-2902-B and a cover page.
Sharma, S. et al., "Isolation, purification and properties of tannase from *Aspergillus niger* van Tieghem," World Journal of Microbiol. & Biotechnol., vol. 15, No. 6, 1999, pp. 673-677 and a cover page.
Dhar, S. C. et al., "Purification, Crystallisation and Physico-Chemical Properties of Tannase of *Aspergillus niger*," Leather Science, vol. 11, No. 2, 1964, pp. 27-38.
Pel, H.J., "unnamed protein product [*Aspergillus niger*]", GenBank Accession CAK38707.1, EMBL Accession AM270075.1, Mar. 24, 2007, [retrieved on Oct. 23, 2009J, Retrieved from the Internet: <URL: http://www.ncbi.nlm.nih.gov/protein/134058723> (2 pages).
Mahapatra, K. et al., "Purification, characterization and. some studies on secondary structure of tannase from *Aspergillus awamori nakazawa*," Process Biochem., vol. 40, 2005, pp. 3251-3254.
International Search Report dated Nov. 10, 2009, issued for PCT/JP2009/005105.
Kalyani Mahapatra et al., "Purification, characterization and some studies on secondary structure of tannase from *Aspergillus awamori nakazawa*," Process Biochemistry 40, 2005, pp. 3251-3254.
Office Action dated Mar. 12, 2012, issued for the Chinese patent application No. 200980142179.1.

* cited by examiner

*Primary Examiner* — Tekchand Saidha
(74) *Attorney, Agent, or Firm* — Edwards Wildman Palmer LLP; James E. Armstrong, IV; Edmund J. Koundakjian

(57) ABSTRACT

Disclosed is a thermostable tannase derived from a microorganism. Specifically disclosed is a thermostable tannase derived from *Aspergillus awamori* or *Aspergillus niger*. A preferred embodiment of the tannase has the following chemoenzymatic properties: (1) activity: to act on a depside bond to thereby cause hydrolysis; (2) molecular weight: about 230,000 Da (as measured by gel filtration); and (3) thermal stability: stable at a temperature up to 65° C. (pH 5.0, 30 min.)

8 Claims, 5 Drawing Sheets

TANNASE, GENE ENCODING SAME, AND PROCESS FOR PRODUCING SAME

TECHNICAL FIELD

The present invention relates to novel tannase produced by a microorganism belonging to the genus *Aspergillus*. Specifically, the invention relates to tannase produced by the genus *Aspergillus*, which is excellent in thermostability, a gene encoding the tannase, a process for producing the tannase, a use of the tannase, and the like.

BACKGROUND ART

Tannase (tannin acyl hydrolase, EC3.1.1.20) is an enzyme that hydrolyzes a depside bond of tannins. In the food industry, tannase is used for prevention of cream down in tea beverages, prevention of lee in fruit juice beverages, clarification of beer, and the like.

Production of tannase by bacteria, yeasts, and filamentous fungi has been reported in large numbers so far (Non-patent Document 1). There are many reports about the genus *Aspergillus* and the genus *Penicillium* for the filamentous fungi. Chemoenzymatic properties, an amino acid sequence and a gene encoding tannase have been revealed for tannase derived from *Aspergillus oryzae* (see Patent Documents 1 and 2, and Non-patent Document 2).

The tannase described in Patent Document 1 has mild acidity such as an optimum pH range around from 5.0 to 5.5, and an optimum temperature range of around 40° C., and is deactivated within 10 minutes at a high temperature such as higher than 60° C. Therefore, the tannase is reacted under very limited conditions in industrial applications. The tannase described in Patent Document 2 is excellent in thermostability, a residual activity after treatment at 65° C. for 10 minutes in a citric acid buffer solution (pH 5.5) is 80% or more, and an optimum temperature range is from 60 to 80° C., and thus, the defect of the tannase described in Patent Document 1 is overcome, but production of a recombinant was only reported and production of a non-recombinant is not confirmed. Therefore, for applications in the food industry, safety confirmation according to "safety evaluation standard of additives produced in use of genetically modified organisms" is required (Non-patent Document 3). In addition, there is deep-seated rejection against genetically modified foods in Japan. Accordingly, the tannase cannot be recognized as one that is immediately applicable in the food industry.

On the other hand, tannase excellent in thermostability, which has an optimum temperature of 60° C. or higher, (see Non-patent Documents 4 and 5) was also reported. However, existence of such tannase has been merely confirmed and the amino acid sequence thereof, a gene encoding the tannase, chemoenzymatic properties thereof, and the like have not been revealed and a practical application has not been achieved yet.

PRIOR ART DOCUMENTS

Patent Documents

Patent Document 1: Japanese Patent Application Unexamined Publication No. 8-80196
Patent Document 2: Japanese Patent Application Unexamined Publication No. 2003-250588

Non-Patent Documents

Non-patent Document 1: Appl. Microbiol. Biotechnol., Vol. 76, pp. 47-59, 2007

Non-patent Document 2: Gene, Vol. 175, pp. 215-221, 1996
Non-patent Document 3: Food Safety Commission "Safety evaluation standard of additives produced in use of genetically modified organisms" determined on Mar. 25, 2004
Non-patent Document 4: Microbiology, Vol. 149, pp. 2941-2946, 2003
Non-patent Document 5: Process Biochemistry, Vol. 40(5), April 2005, pp. 1553-1557, 2005

SUMMARY OF THE INVENTION

Problems to be Solved by the Invention

An object of the present invention is to provide tannase excellent in thermostability, which is derived from microorganisms existing in the natural world. Another object of the invention is also to provide a gene of the tannase, a process for producing the tannase and a use of the tannase.

Means for Solving the Problems

The present inventors have intensively investigated in order to solve the above-mentioned problems. As a result, production of tannase having high thermostability was observed in totally 5 strains that are 3 strains of *Aspergillus niger* and 2 strains of *Aspergillus awamori*. Further investigations proceeded and the present inventors succeeded in isolation of tannase produced by *Aspergillus awamori* NBRC-4033 (IFO-4033) and determined the chemoenzymatic properties thereof. They also succeeded in identification of the amino acid sequence of the tannase and a base sequence of a gene encoding the tannase. As a result of comparing the chemoenzymatic properties and the amino acid sequence to those of tannase previously reported, the tannase successfully obtained and identified was confirmed to be novel.

The present invention was accomplished based on the above-mentioned achievements, and is shown as follows.

[1] Tannase derived from *Aspergillus awamori* or *Aspergillus niger*, which is resistant to a thermal treatment at 65° C.

[2] Tannase having the following chemoenzymatic properties:
(1) activity: to act on a depside bond to thereby cause hydrolysis;
(2) molecular weight: about 230,000 Da (as measured by gel filtration); and
(3) thermostability: stable at a temperature up to 65° C. (pH 5.0, 30 min.)

[3] The tannase according to [2], further having the following chemoenzymatic properties:
(4) optimum temperature: about 70° C.;
(5) optimum pH: about 5.5;
(6) pH stability: stable within the range from pH 3 to 8 (30° C., 30 min.); and
(7) substrate specificity: preferably act on tannic acid, and act on gallic acid esters.

[4] The tannase according to [2] or [3], derived from *Aspergillus awamori*.

[5] Tannase having the amino acid sequence set forth in SEQ ID NO: 5 or an amino acid sequence equivalent to the amino acid sequence set forth in SEQ ID NO: 5.

[6] The tannase according to [5], wherein the equivalent amino acid sequence is 90% or more identical to the amino acid sequence set forth in SEQ ID NO: 5.

[7] An enzyme preparation containing the tannase according to any one of [1] to [6] as an active ingredient.

[8] A tannase gene containing one of DNA selected from the group consisting of the following (A) to (C):

(A) DNA encoding the amino acid sequence set forth in SEQ ID NO: 5;

(B) DNA having the base sequence set forth in SEQ ID NO: 4; and (C) DNA having a base sequence equivalent to the base sequence set forth in SEQ ID NO: 4 and encoding a protein having a tannase activity.

[9] A recombinant vector containing the tannase gene according to [8].

[10] A transformant into which the tannase gene according to [8] has been introduced.

[11] A process for producing tannase, including the following steps (1) and (2), or the following steps (i) and (ii):

(1) culturing a microorganism selected from the group consisting of *Aspergillus awamori* and *Aspergillus niger*; and (2) collecting tannase from the culture solution and/or the cell body after the culture, (i) culturing the transformant according to [10] under the conditions in which the protein encoded by the gene is produced; and (ii) collecting the produced protein.

[12] The process for producing tannase according to [11], wherein the microorganism is *Aspergillus awamori* NBRC-4033 (IFO-4033).

[13] A hydrolysis process, wherein tannase according to any one of [1] to [6], the enzyme preparation according to [7], or tannase obtained in the production process according to [11] or [12] acts on tannin or a tannin-containing composition.

DESCRIPTION OF EMBODIMENTS (Terms)

Figure 1:
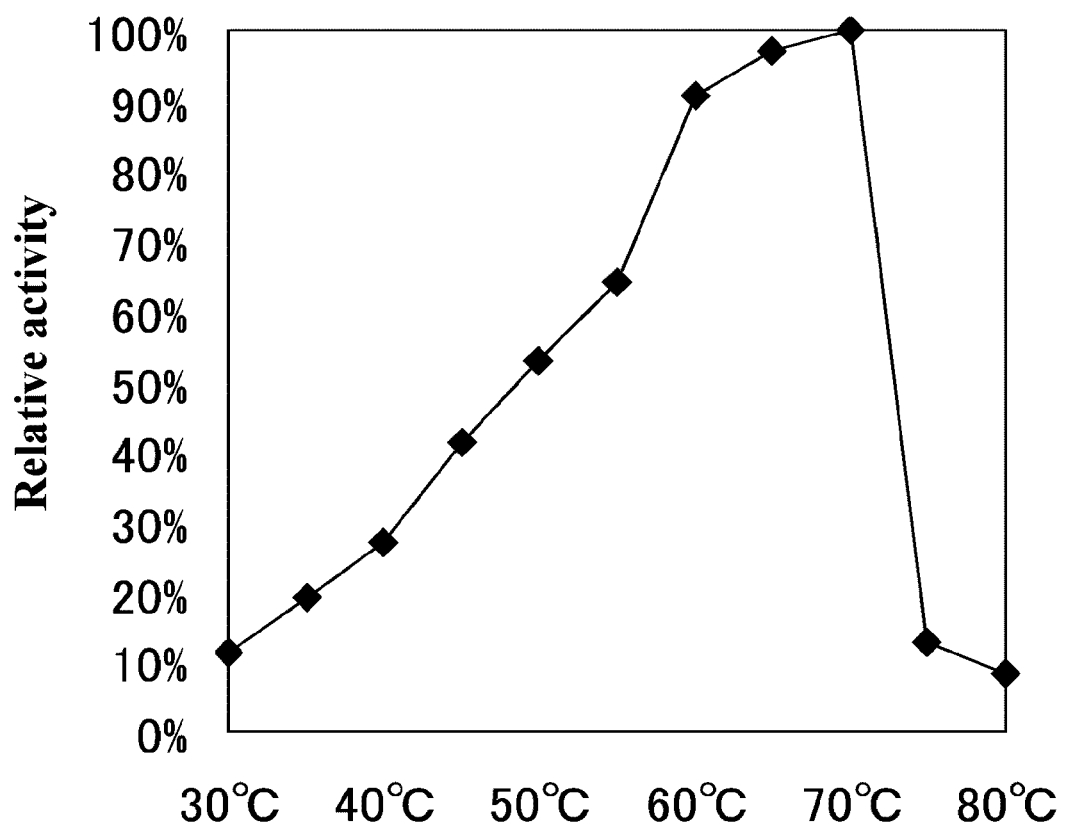
FIG. 1 is a graph showing an optimum temperature of tannase derived from *Aspergillus awamori*.

The term "DNA encoding protein" in the present invention denotes DNA from which the protein is obtained when it is expressed, that is, DNA having a base sequence corresponding to an amino acid sequence of the protein. Therefore, the codon degeneracy is also taken into consideration.

In the present specification, the term "isolated" and "purified" are used interchangeably. The term "isolated" used with respect to the enzyme of the present invention tannase), which is derived from a natural material, denotes a state in which components other than the enzyme are not substantially contained (in particular, contaminated protein is not substantially contained) in the natural material. Specifically, in the isolated enzyme of the present invention, the content of the contaminant protein is, for example, less than about 20%, preferably less than about 10%, further preferably less than about 5%, and yet further preferably less than about 1% with respect to the total amount on the weight basis. On the other hand, the term "isolated" when the enzyme of the present invention is prepared by genetically engineering technique denotes a state in which other components derived from a host cell to be used, a culture solution, and the like, are not substantially contained. Specifically, for example, in the isolated enzyme of the present invention, the content of the contaminant components is less than about 20%, preferably less than about 10%, further preferably less than about 5%, and yet further preferably less than about 1% with respect to the total amount on the weight basis. Unless otherwise specified, when merely the term "tannase" is used in this specification, it signifies the "tannase in an isolated state." The same is true to the term "the present enzyme" used instead of tannase.

The term "isolated" used with respect to DNA denotes typically that DNA is separated from other nucleic acid coexisting in nature when the DNA originally exists in nature. However, some of the other nucleic acid components such as a neighboring nucleic acid sequence in nature (for example, a sequence of a promoter region, a terminator sequence, or the like) may be included. For example, in the "isolated" state of the genome DNA, the isolated DNA preferably does not substantially include other DNA components coexisting in nature. On the other hand, in the "isolated" state of DNA prepared by a genetic engineering technique, for example, a cDNA molecule, and the like, preferably, the DNA does not substantially include cell components, a culture solution, or the like. Similarly, in the "isolated" state in the case of DNA prepared by chemical synthesis, the DNA does not include a precursor (a raw material) or chemical materials used in synthesis, for example, dNTP. Unless otherwise specified, when merely the term "DNA" is used in this specification, it signifies the "DNA in an isolated state."

(Tannase and Producing Microorganism Thereof)

A first aspect of the present invention provides tannase (hereinafter, also referred to as "the present enzyme") and the producing microorganism thereof. As shown in examples mentioned below, the present inventors have intensively investigated; as a result, they found that *Aspergillus awamori* and *Aspergillus niger* produced thermostable tannase resistant to a thermal treatment at 65° C. Further investigations proceeded and the present inventors succeeded in separation and purification of tannase derived from *Aspergillus awamori*, and at the same time, succeeded in determination of the chemoenzymatic properties thereof as shown below.

(1) Action

The present enzyme is tannase and acts on a depside bond to hydrolyze the depside bond.

(2) Molecular Weight

The present enzyme shows a molecular weight of about 230,000 Da by gel filtration. The present enzyme shows a molecular weight of 90,000 to 100,000 Da by SDS-PAGE. The present enzyme has a sugar chain and shows significant decrease in the molecular weight by an endoglycosidase H (EndoH) treatment.

(3) Thermostability

The present enzyme maintains 90% or more of the activity in 50 mM citric acid buffer solution (pH 5.0) at 65° C. for 30 minutes.

(4) Optimum Temperature

The optimum temperature of the present enzyme is about 70° C. The present enzyme shows high activity at a temperature in the range from about 60° C. to about 70° C. The optimum temperature is a value calculated by the below-mentioned measurement method of tannase activity (50 mM citric acid buffer solution (pH 5.0)).

(5) Optimum pH

The optimum pH of the present enzyme is about 5.5. The present enzyme shows high activity in the range from pH about 5.0 to about 6.0. The optimum pH is determined, for example, based on the results of the measurement in a citric acid buffer with respect to pH region of pH 3 to 6 and based on the results of the measurement in a phosphate buffer with respect to pH region of pH 6 to 8.

(6) pH Stability

The enzyme shows stable activity in such a wide pH range as pH 3 to 8. That is to say, when pH of an enzyme solution subjected to treatment is within the range, the enzyme shows 80% or more activity with respect to the maximum activity after treatment at 30° C. for 30 minutes. The pH Stability is determined, for example, based on the results of the measurement in a citric acid buffer for the pH region of pH 3 to 6, and based on the results of the measurement in a phosphate buffer for the pH region of pH 6 to 8.

(7) Substrate Specificity

The present enzyme preferably acts on tannic acid. The enzyme also acts on gallic acid esters (methyl gallate, ethyl gallate, etc.). In addition, reactivity and substrate specificity of the present enzyme can be measured and evaluated by methods shown in examples mentioned below (sections for measurement method of tannase activity and measurement method of substrate specificity).

Preferably, the present enzyme is tannase derived from *Aspergillus awamori*. Herein, the "tannase derived from *Aspergillus awamori*" denotes tannase produced by microorganisms classified in *Aspergillus awamori* (which may be wild-type strain and mutant strain), or tannase produced by using a tannase gene of *Aspergillus awamori* (which may be wild-type strain and mutant strain) obtained by a genetic engineering technique. Therefore, the "tannase derived from *Aspergillus awamori*" includes a recombinant produced by using a host microorganism into which a tannase gene (or a gene obtained by modifying the gene) obtained from *Aspergillus awamori* has been introduced.

*Aspergillus awamori* from which the present enzyme is derived is represented by a producing microorganism of the present enzyme for easy description.

As mentioned above, the details of the property of the present enzyme that has been successfully obtained has been clarified. As a result, it has been revealed that the present enzyme is excellent in thermostability and excellent in pH Stability. Therefore, the present enzyme is useful for food processing and saccharification.

The present inventors have further investigated and, as a result, have determined an amino acid sequence (SEQ ID NO: 5) of tannase produced by *Aspergillus awamori*. Thus, one embodiment of the present invention is characterized in that the present enzyme consists of a protein having an amino acid sequence set forth in SEQ ID NO: 5. Herein, in general, when a part of the amino acid sequence of a certain protein is modified, the modified protein may sometimes have a function the same as that of the protein before modification. That is to say, the modification of the amino acid sequence does not have a substantial effect on the function of the protein, so that the function of the protein may be maintained before and after the modification. As another embodiment, the present invention provides a protein having an amino acid sequence equivalent to the amino acid sequence set forth in SEQ ID NO: 5 and having the tannase activity (hereinafter, which is referred to as "equivalent protein"). The "equivalent amino acid sequence" herein denotes an amino acid sequence that is partly different from the amino acid sequence set forth in SEQ ID NO: 5 but this difference does not have a substantial effect on the function (herein, the tannase activity) of the protein. "Having the tannase activity" denotes an activity of acting on a molecule having a depside bond such as, typically, tannic acid; and gallic acid esters, digallic acid, gallotannin and ellagitannin to hydrolyze the depside bond; however, the degree of the activity is not particularly limited as long as the function of tannase can be exhibited. However, it is preferable that the activity is equal to or higher than that of the protein having the amino acid sequence set forth in SEQ ID NO: 5.

The "partial difference in the amino acid sequence" typically denotes that mutation (change) occurs in an amino acid sequence due to deletion or substitution of one to several amino acids constituting the amino acid sequence, or addition or insertion of one to several amino acids, or the combination thereof. Herein, the difference in the amino acid sequence is permitted as long as the tannase activity is maintained (more or less change in the activity is permitted). As long as this condition is satisfied, the position in which a difference in the amino acid sequence occurs is not particularly limited and the difference may occur in a plurality of positions. The plurality herein signifies a numerical value corresponding to less than about 30%, preferably less than about 20%, further preferably less than about 10%, still further preferably less than about 5%, and most preferably less than about 1% with respect to the total amino acid. That is to say, the equivalent protein has, for example, about 70% or more, preferably about 80% or more, further preferably about 90% or more, still further preferably about 95% or more and most preferably about 99% or more identity to the amino acid sequence set forth in SEQ ID NO: 5.

Preferably, an equivalent protein is obtained by allowing conservative amino acid substitution to be generated in an amino acid residue that is not essential to the tannase activity. Herein, "conservative amino acid substitution" denotes substitution of an amino acid residue to an amino acid residue having a side chain of the same property. The amino acid residue is classified into some families according to its side chain, for example, the basic side chain (for example, lysin, arginine, and histidine), the acid side chain (for example, asparatic acid, and glutamic acid), the uncharged polar side chain (for example, glycine, asparagine, glutamine, serine, threonine, tyrosine, and cysteine), the nonpolar side chain (for example, alanine, valine, leucine, isoleucine, proline, phenyl alanine, methionine, and tryptophane), β branched side chain (for example, threonine, valine, and isoleucine), and the aromatic side chain (for example, tyrosine, phenyl alanine, tryptophane, and histidine). The conservative amino acid substitution is carried out between the amino acid residues in the same family.

The "equivalent protein" may have an additional property. Examples of such a property include a property that stability is more excellent than the protein including the amino acid sequence set forth in SEQ ID NO: 5, a property that function that is different only at low temperature and/or high temperature is exhibited, and a property that an optimum pH is different.

The identity (%) between two amino acid sequences or two nucleic acids (hereinafter, referred to as "two sequences" as a term including the both) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain a nucleotide sequence equivalent to the nucleic acid molecule of the present invention, for example, BLAST nucleotide search with score=100 and word length=12 may be carried out by the NBLAST program. In order to obtain an amino acid sequence equivalent to the polypeptide molecule of the present invention, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. Furthermore, the homology between two nucleic acid sequences can be determined using the GAP program in the GCG software package (available at http://www.gcg.com) with the gap weight of 50 and the gap length weight of 3.

The present enzyme may be a part of a larger protein (for example, fusion protein). Examples of a sequence to be added in the fusion protein may include a sequence useful for purification, for example, a sequence of a multi histidine residue, and an additional sequence for securing the safety for producing a recombinant, and the like.

The present enzyme having the above-mentioned amino acid sequence can be prepared easily by a genetic engineering technique. For example, the present enzyme can be prepared by transforming an appropriate host cell (for example, *Escherichia coli*) by DNA encoding the present enzyme, and by collecting proteins expressed in the transformant. The collected proteins are appropriately purified according to the purposes. In the case where the present enzyme is prepared as a recombinant protein, various modifications can be carried out. For example, DNA encoding the present enzyme and other appropriate DNA are inserted into the same vector and the vector is used for producing a recombinant protein. Then, the enzyme consisting of a recombinant protein to which arbitrary peptide or protein is linked can be obtained. Furthermore, modification may be carried out so as to cause addition of sugar chain and/or lipid or processing of N-terminal or C-terminal. The above-mentioned modification permits extraction of a recombinant protein, simplification of purification, addition of biological functions, or the like.

(DNA Encoding Tannase)

A second aspect of the present invention provides a gene encoding the present enzyme, that is, a novel tannase gene. In one embodiment, the gene of the present invention includes DNA encoding the amino acid sequence set forth in SEQ ID NO: 5. A specific example of this embodiment is a DNA consisting of the base sequence set forth in SEQ ID NO: 4.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the base sequence set forth in SEQ ID NO: 4 and having the tannase activity (hereinafter, which is also referred to as "equivalent DNA"). The "equivalent base sequence" herein denotes a base sequence which is partly different from the base sequence set forth in SEQ ID NO: 4 but in which the function (herein, tannase activity) of the protein encoded by the sequence is not substantially affected by the difference.

A specific example of the equivalent DNA includes DNA that hybridizes to the complementary base sequence of the base sequence of SEQ ID NO: 4 under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5× Denhardt solution, 1% SDS, 10% dextran sulfate, 10 μg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1× Denhardt solution, 1% SDS, 10% dextran sulfate, 10 μg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases when the base sequence of SEQ ID NO: 4 is a reference base sequence, and which has a tannase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA. The above-mentioned equivalent DNA can be obtained by modifying DNA having the base sequence shown in SEQ ID NO: 4 so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in base as mentioned above due to polymorphism represented by SNP (single nucleotide polymorphism).

The gene of the present invention can be prepared in an isolated state by using a standard genetic engineering technique, a molecular biological technique, a biochemical technique, and the like, with reference to sequence information disclosed in the present specification or attached sequence list. Specifically, the gene of the present invention can be prepared by appropriately using oligonucleotide probe/primer capable of specifically hybridizing to the gene of the present invention from an appropriate genome DNA library or a cDNA library of *Aspergillus awamori*, or cell body extract of *Aspergillus awamori*. An oligonucleotide probe/primer can be easily synthesized by using, for example, a commercially available automated DNA synthesizer. As to a production method of libraries used for preparing the gene of the present invention, see, for example, Molecular Cloning, Third Edition, Cold Spring Harbor Laboratory Press, New York.

For example, a gene having the base sequence set forth in SEQ ID NO: 4 can be isolated by using a hybridization method using all or a part of the base sequence or its complimentary sequence as a probe. Furthermore, amplification and isolation can be carried out by using a nucleic acid amplification reaction (for example, PCR) using a synthesized oligonucleotide primer designed to specifically hybridize to a part of the base sequence. Furthermore, it is possible to obtain a target gene by chemical synthesis based on the information of the amino acid sequence set forth in SEQ ID NO: 5 or the base sequence set forth in SEQ ID NO: 4 (see, reference document: Gene, 60(1), 115-127 (1987)).

Hereinafter, a specific example of the method of obtaining the gene of the present invention is described. Firstly, the present enzyme (tannase) is isolated and purified from *Aspergillus awamori*, and information about the partial amino acid sequence is obtained. As a method for determining the partial amino acid sequence thereof, for example, purified tannase is directly subjected to amino acid sequence analysis [protein-sequencer 476A, Applied Biosystems] by Edman Degradation [Journal of biological chemistry, vol. 256, pages 7990-7997 (1981)] according to a routine method. It is effective that limited hydrolysis is carried out by allowing protein hydrolase to act, the obtained peptide fragment is separated and purified, and the thus obtained purified peptide fragment is subjected to the amino acid sequence analysis.

Based on the information of thus obtained partial amino acid sequence, a tannase gene is cloned. Cloning can be carried out by using, for example, a hybridization method or a PCR method. When the hybridization method is used, for example, a method described in Molecular Cloning (Third Edition, Cold Spring Harbor Laboratory Press, New York) can be used.

When the PCR method is used, the following method can be used. Firstly, PCR reaction is carried out by using a synthesized oligonucleotide primer designed based on the information of the partial amino acid sequence using a genome DNA of a microorganism producing tannase as a template, and thus a target gene fragment is obtained. The PCR method is carried out according to the method described in PCR Technology, edited by Erlich. H A, Stocktonpress, 1989]. Furthermore, when a base sequence is determined by a method usually used in the amplification DNA fragment, for example, a dideoxy chain terminator method, a sequence corresponding to the partial amino acid sequence of tannase other than the sequence of the synthesized oligonucleotide primer is found in the determined sequence, and a part of the tannase gene can be obtained. When a hybridization method and the like is further carried out by using the obtained gene fragment as a probe, a gene encoding the full length of the tannase can be cloned.

In the below mentioned Examples, a sequence of a gene encoding tannase produced by *Aspergillus awamori* is determined by using the PCR method. The complete base sequence of a gene encoding tannase produced by *Aspergillus awamori* is shown in SEQ ID NO: 4. Furthermore, the amino acid sequence encoded by the base sequence is determined (SEQ ID NO: 5). In addition to the base sequence shown in SEQ ID NO:4, a plurality of the base sequences corresponding to the amino acid sequence set forth in SEQ ID NO: 5 are present.

All or a part of the tannase gene (SEQ ID NO: 4) whose complete base sequence has been clarified is used as a probe of hybridization, and thereby DNA having high homology with respect to the tannase gene of SEQ ID NO: 4 can be selected from a genome DNA library or a cDNA library of microorganisms producing other tannase.

Similarly, a primer for PCR can be designed. By carrying out PCR reaction using this primer, a gene fragment having high homology with respect to the above-mentioned tannase gene can be detected and, furthermore, a complete gene thereof can be obtained.

Protein of the obtained gene is manufactured, and its tannase activity is measured. Thereby, it is possible to confirm whether or not the obtained gene is a gene encoding a protein having the tannase activity. Furthermore, by comparing the base sequence (or the amino acid sequence encoded thereby) of the obtained gene with the base sequence (or the amino acid sequence encoded thereby) of the above-mentioned tannase gene, the gene structure or the homology may be examined, thereby determining whether or not the gene encodes protein having the tannase activity.

Since the primary structure and the gene structure are clarified, modified tannase (a gene subjected to at least one of deletion, addition, insertion, and substitution of one or a plurality of amino acid residues) can be obtained by introduction of random mutation or site-specific mutation. This makes it possible to obtain a gene encoding tannase that has a tannase activity but has different optimum temperature, thermostability, optimum pH, stable pH, substrate specificity, and the like. Furthermore, it becomes possible to manufacture modified tannase by genetic engineering.

Herein, a scheme for introducing mutation is carried out with consideration of, for example, a characteristic sequence of a gene sequence. The consideration of a characteristic sequence can be made by considering, for example, the prediction of the three-dimensional structure of the protein, and homology to existing proteins.

Examples of the method for introducing random mutation include: a method, as method of chemically treating DNA, which causes transition mutation in which sodium hydrogensulfite is allowed to act and cytosine base is converted into uracil base [Proc. Natl. Acad. Sci. U.S.A., 79, 1408-1412 (1982)]; a method, as a biochemical method, which causes base substitution during the process of synthesizing the double strand in the presence of [α-S]dNTP [Gene, vol 64, pages 313-319 (1988)]; a method, as a method of using PCR, which carries out PCR in a reaction system with manganese added, thereby lowering fidelity of incorporation of nucleotides [Anal. Biochem., 224, 347-353 (1995)], and the like.

Examples of the method for introducing site-specific mutation include a method using amber mutation [gapped duplex method; Nucleic Acids Res., Vol. 12, No. 24, 9441-9456 (1984)]; a method using a recognition site of the restriction enzyme [Analytical Biochemistry, Vol. 200, pages 81-88 (1992), Gene, Vol. 102, pages 67-70 (1991)]; a method using mutation of dut (dUTPase) and ung (uracil-DNA glycosilase) [Kunkel method; Proc. Natl. Acad. Sci. U.S.A., 82, 488-492 (1985)]; a method using amber mutation using DNA polymerase and DNA ligase [Oligonucleotide-directed Dual Amber: ODA) method, Gene, Vol. 152, pages 271-275 (1995), Japanese Patent Application Unexamined Publication No. H7-289262]; a method using a host inducing a repair system of DNA (Japanese Patent Application Unexamined Publication No. H8-70874); a method using a protein catalyzing a DNA strand exchange reaction (Japanese Patent Application Unexamined Publication No. H8-140685); a method by PCR using two types of primers for introducing a restriction enzyme into which the recognition site is added (U.S. Pat. No. 5,512,463); a method by PCP using a double strand DNA vector having inactivated drug-resistant gene and two types of primers [Gene, Vol. 103, pages 73-77 (1991)]; a method by PCR using amber mutation [International Publication WO98/02535], and the like.

The site-specific mutation can be easily introduced by using commercially available kits. Examples of the commercially available kits include Mutan-G (register trade mark, Takara Bio Inc.) using the gapped duplex method, Mutan-K (register trade mark, Takara Bio Inc.) using the Kunkel method, Mutan—ExpressKm (register trade mark, Takara Bio Inc.) using the ODA method, QuikChange™ Site-Directed Mutagenesis Kit [STRATAGENE] using a primer for introducing mutation and DNA polymerase derived from *Pyrococcus furiosus*, and the like. Furthermore, as the kits using the PCR method, for example, TaKaRa LA PCR in vitro Mutagenesis Kit (Takara Bio Inc.), Mutan (register trade mark)—Super Express Km (Takara Bio Inc.), and the like.

Thus, the primary structure and the gene structure of tannase are provided by the present invention. As a result, it is possible to genetically manufacture proteins having a tannase activity with high purity at low cost.

(Recombinant Vector)

Another aspect of the present invention relates to a recombinant vector containing the gene of the present invention. The term "vector" as used in this specification is intended to refer to a nucleic acid molecule capable of transporting nucleic acid that is inserted in the vector to the inside of the target such as cells. The types or forms of vector are not particularly limited. Therefor, examples of the vector may be in a form of a plasmid vector, a cosmid vector, a phage vector, a viral vector (e.g., an adenovirus vector, an adeno-associated virus vector, a retrovirus vector, a herpes virus vector, etc).

According to the purpose of use (cloning, protein expression), and by considering the types of host cells, an appropriate vector is selected. Specific examples of the vector include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec1, pMFa, pYES2, etc.), a vector using insect cells as a host (pAc, pVL, etc.), a vector using mammalian cells as a host (pCDM8, pMT2PC, etc.), and the like.

The recombinant vector of the present invention is preferably an expression vector. The term "expression vector" is a vector capable of introducing the nucleic acid inserted therein into the target cells (host cells) and being expressed in the cells. The expression vector usually includes a promoter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the gene of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, New York, a already-known method using restriction enzyme and DNA ligase).

(Transformant)

The present invention further relates to a transformant into which the gene of the present invention is introduced. In the transformant of the preset invention, the gene of the present invention exists as an exogenous molecule. Preferably, the transformant of the present invention can be prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast—polyethylene glycol method (Yelton, M. M. et al., Proc. Natl. Acad. Sci. 81, 1470-1474 (1984)), and the like.

Examples of the host cell may include microorganism, animal cells, plant cells, and the like. Examples of microorganisms may include bacterial cells such as *Escherichia coli*, *Bacillus* sp., *Streptomyces* sp., and *Lactococcus* sp.; yeast such as *Saccharomyces* sp., *Pichia* sp., and *Kluyveromyces* sp.; filamentous fungi such as *Aspergillus* sp., *Penicillium* sp., and *Trichoderma* sp. As the animal cell, baculovirus may be used.

(Process for Producing Tannase)

A further aspect of the present invention provides a process for producing tannase. In one embodiment of the invention, a step of culturing a microorganism selected from the group consisting of *Aspergillus awamori* and *Aspergillus niger* (step (1)) and a step of collecting tannase from the culture solution and/or the cell body after the culture (step (2)) are carried out. As shown in examples mentioned below, according to investigations made by the present inventors, *Aspergillus awamori* (No. 1725, NBRC-4033 in Table 3) and *Aspergillus niger* (No. 1332, No. 1349, No. 1363 in Table 3) were found as tannase-producing strains excellent in thermostablity. In the production process of the present invention, the step (1) is preferably carried out using one of these microorganisms. The step (1) is more preferably carried out using *Aspergillus awamori* NBRC-4033 (IFO-4033) that highly produces tannase excellent in thermostability. A culturing method and culturing conditions are not particularly limited as long as the targeted enzyme can be produced. That is to say, a method and culturing conditions which are appropriate for culturing microorganisms to be used can be suitably set on the condition that the present enzyme is produced. As the culturing method, either of liquid culture or solid culture may be used, but liquid culture is preferably used. As liquid culture is exemplified, the culturing conditions thereof will be explained.

Any media can be used as long as microorganisms to be used can grow. For example, a medium containing a carbon source such as glucose, sucrose, gentiobiose, soluble starch, glycerin, dextrin, syrup, and organic acids; a nitrogen source such as ammonium sulfate, ammonium carbonate, ammonium phosphate, ammonium acetate, or peptone, yeast extract, corn steep liquor, casein hydrolysate, bran, meat extract, and the like; and further, inorganic salts such as potassium salt, magnesium salt, sodium salt, phosphate salt, manganese salt, iron salt, and zinc salt, can be used. In order to promote the growth of microorganisms to be used, vitamin, amino acid, and the like may be added to the medium. Tannic acid can be added to a medium in order to induce production of tannase. The pH of the medium is adjusted to, for example, about 3 to 10, and preferably, about 5 to 6. The culturing temperature is generally about 10° C. to 50° C., and preferably about 27° C. to 33° C. The culturing is carried out for one to seven days, preferably three to four days under aerobic conditions. As a culturing method, for example, a shake culture method, and an aerobic submerged culture method with a jar fermenter can be employed.

After the culturing in the above-mentioned conditions, tannase is collected from the culture solution or the cell body (step (2)). When tannase is collected from the culture solution, the present enzyme can be obtained by separation and purification after removing insoluble matters by, for example, filtration, centrifugation of culture supernatant followed by carrying out any combinations of concentration by ultrafiltration, salting out of ammonium sulfate precipitation, dialysis, various types of chromatography such as ion-exchange resin, and the like.

On the other hand, when the present enzyme is collected from the cell body, the present enzyme can be obtained by pulverizing the cell body by pressuring treatment, ultrasonication, and the like, followed by separation and purification thereof similar to the above. Note here that the above-mentioned series of processes (pulverizing, separation, and purification of cell body) may be carried out after the cell body is collected from a culture solution by filtration, centrifugation, and the like. Furthermore, the final form may be a liquid state or a solid state (including a powder state). Note here that confirmation of expression or confirmation of expression product can be carried out easily by using an antibody against tannase, but expression can also be confirmed by measuring the tannase activity.

According to another embodiment of the present invention, tannase is manufactured by using the above-mentioned transformant. In the manufacturing method in this embodiment, firstly, the above-mentioned transformant is cultured in the conditions in which the protein encoded by the introduced gene is produced (step (i)). As to various vector-host systems, the culture conditions for transformant are well-known, and a person skilled in the art can set appropriate culture conditions easily. After the culturing step, a step of collecting the produced protein (i.e., tannase) is carried out (step (ii)). Collection and the following purification may be carried out by the same method as mentioned in the above-mentioned embodiment.

(Enzyme Preparation)

The present enzyme is provided in a form of, for example, an enzyme preparation. The enzyme preparation may contain, in addition to an active ingredient (the enzyme of the present invention), excipient, buffer agents, suspension agents, stabilizer, preservatives, antiseptics, physiologic saline, and the like. Examples of the excipient may include lactose, sorbitol, D-mannitol, sucrose, and the like. Examples of the buffer agent may include phosphate, citrate, acetate, and the like. Examples of the stabilizer may include propylene glycol, and ascorbic acid, and the like. Examples of the preservative may include phenol, benzalkonium chloride, benzyl alcohol, chlorobutanol, methyl paraben, and the like. Examples of the antiseptic may include benzalkonium chloride, parahydroxybenzoate, chlorobutanol, and the like.

(Applications of Tannase)

A further aspect of the present invention provides a hydrolysis process of using the present enzyme (or an enzyme preparation containing the enzyme) as an application of the present enzyme. In the hydrolysis process of the present invention, the present enzyme (or an enzyme preparation containing the enzyme) is allowed to act on tannin or a composition containing tannin. The hydrolysis process of the invention is effective to improvement in quality of foods containing tannin. For example, the hydrolysis process is used for prevention of cream down in tea beverages, prevention of precipitation (lee) and opacity in fruit juice beverages or vegetable juice beverages, beer, or the like. The "tea beverages" herein denote beverages containing an extracted component of tea leaves or plants other than tea leaves. Examples of the tea beverages include green tea, black tea, oolong tea, du zhong tea, and herbal tea or the like. The "fruit juice beverages" denote beverages produced using fruit juice obtained by squeeze of fruits. In the same manner, the "vegetable juice beverages" denote beverages produced using vegetable juice. The "beer beverages" include beer, sparkling liquor, and alcoholic beverages having flavors and feeling of a drink similar to those of beer (such as so-called the third category beer that is classified into the other miscellaneous alcohols and liqueurs on liquor tax). Note here that drinks to which the hydrolysis process of the present invention is applied are not limited to the above-mentioned examples. For example, the hydrolysis process of the present invention can also be applied to improvement in quality of fruit juice-containing tea beverages, vegetable and fruit juice beverages using fruit juice and vegetable juice, etc.

The present enzyme has a stably acting wide pH range as described above. That is, the present enzyme is stable within the range from pH 3.0 to 8.0, and can be used in foods, etc. in mild acid and neutral regions. A pH of a tea beverage is in the neutral region and a pH of a fruit juice beverage is in the mild acid region, and the present enzyme favorably acts on the both beverages. On the other hand, since the optimum temperature of the present enzyme is 60 to 70° C., a reaction can be carried out at the same time of heat extraction from tea leaves, for example. Furthermore, the present enzyme satisfies a demand such that "a reaction at a high temperature is desirable from the viewpoint of corruption prevention". In addition, the present enzyme is rapidly deactivated in a general heat sterilization condition (for example, 95° C. or higher) in a production step of drinks, and thus, a particular heating step for deactivation of the present enzyme is not required. However, it does not prevent providing the heating step for deactivation of the present enzyme.

EXAMPLES

<Measurement Method of Tannase Activity>

As described below, the method of Deschamps (J. Ferment. Technol. 61 [1] 55-59, 1983) was modified and an activity of tannase was measured.

0.5 mL of a 50 mM citric acid buffer solution (pH 5.0) containing 1% tannic acid (Tannic acid, ACS Reagent [SIGMA]) is added with 0.5 ml of an enzyme solution, and incubated at 37° C. for 30 minutes, thereafter adding a 0.2 M acetic acid buffer solution (pH 5.0) containing 2% BSA to terminate the reaction. After terminating the reaction, the reaction solution is stood still in ice for 20 minutes and then centrifuged at 3,000 rpm for 20 minutes. The obtained supernatant is diluted 50 holds and an absorbance at a wavelength of 260 nm is measured. An analytical curve (standard curve) is formed using gallic acid and an enzyme amount that releases 1 μM of gallic acid for 1 minute is assumed to be 1 unit.

<Measurement Method of Substrate Specificity>

As described below, the method of Sharma (Anal. Biochem. 279, 85-89, 2000) was modified and substrate specificity was measured.

125 μL of a 50 mM citric acid buffer solution (pH 5.0) containing 0.17% tannic acid or 10 mM gallic acid esters (methyl gallate, ethyl gallate, propyl gallate, and isoamyl gallate) is added with 125 μL of an enzyme solution and incubated at 37° C. for 30 minutes, followed by adding and mixing 300 μL of methanol containing 0.667% Rhodanine, and the reaction solution is stood still for 10 minutes. Next, 200 μL of 0.5 N NaOH is added and mixed and the reaction solution is stood still for 10 minutes. Subsequently, the reaction solution is diluted with 9 mL of distilled water and left for 5 minutes, and an absorbance at a wavelength of 520 nm is measured. An analytical curve (standard curve) was formed using gallic acid and an activity that releases 1 μM of gallic acid for 1 minute is assumed to be 1 unit.

1. Screening of Thermo Stable Tannase Producing Microorganism

Among various strains in which tannase activities were observed in an immersion liquid of solid culture or a culture supernatant of liquid culture, presence or absence of production of thermostable tannase was examined for 5 strains belonging to *Aspergillus niger* (1332 strain, 1349 strain, 1363 strain, 9331 strain, and 9340 strain) and 3 strains belonging to *Aspergillus awamori* (1725 strain, 1736 strain, and NBRC-4033 strain). Each strain was cultured at 30° C. on a potato dextrose agar medium (Eiken Chemical Co., Ltd.) for 10 to 14 days until preferable spore formation was attained. The spores formed on the obtained colony was scraped with a sterile spore suspension buffer (0.85% NaCl, 0.05% TWEEN (register trade mark) 80) to prepared a spore suspension. The spore suspension was inoculated into the medium of Table 1 and subjected to shake culture at 30° C. for 3 days. This culture solution was inoculated into the medium of Table 2 and subjected to shake culture at 30° C. for 4 days.

TABLE 1

|  | (w/v) |
|---|---|
| Glucose | 1.0% |
| Polypeptone | 1.0% |
| Yeast extract | 0.5% |
| $KH_2PO_4$ | 0.2% |
| $MgSO_4$ | 0.05% | pH 5.5

TABLE 2

|  | (w/v) |
|---|---|
| Soluble starch | 3.0% |
| Polypeptone | 1.0% |
| Yeast extract | 0.5% |
| KCl | 0.2% |
| $KH_2PO_4$ | 0.1% |
| $MgSO_4$ | 0.05% |
| Tannic acid | 0.2% | pH 6.5

The obtained each culture supernatant was treated at 65° C. for a predetermined time (30 minutes, 60 minutes, and 90 minutes) and a tannase activity was measured by the above-mentioned measurement method of a tannase activity. The measurement results are shown in Table 3. In Table 3, the tannase activity (actual measurement values) of each of the culture supernatants after being treated at 65° C. for 30 minutes, and treating times and change in the residual tannase activities are shown. The residual activity of a treating time of 60 minutes or 90 minutes was shown as a relative value, assuming the residual activity of a treating time of 30 minutes to be the base (100%).

TABLE 3

|  | No. | Tannase activity (Actual value after treatment for 30 min.) units/mL | Treating time | | |
|---|---|---|---|---|---|
|  |  |  | 30 min. | 60 min. | 90 min. |
| *A. niger* | No. 1332 | 1.06 | 100.0% | 103.2% | 95.8% |
|  | No. 1349 | 0.32 | 100.0% | 96.6% | 100.0% |
|  | No. 1363 | 1.31 | 100.0% | 94.6% | 85.1% |
| *A. awamori* | No. 1725 | 2.07 | 100.0% | 91.9% | 91.9% |
|  | NBRC-4033 | 0.44 | 100.0% | 93.2% | 79.5% |

As shown in Table 3, all of the test strains were shown to produce thermostable tannase.

2. Production and Purification of Tannase derived from *Aspergillus awamori* NBRC-4033 (IFO-4033)

The spore suspension of *Aspergillus awamori* NBRC-4033 (IFO-4033) shown in 1. was inoculated into the medium of Table 1 and subjected to shake culture at 30° C. for 3 days. This culture solution was inoculated into the medium of Table 4 and subjected to shake culture at 30° C. for 4 days. The tannase activity of this culture supernatant was 0.35 unit/ml. The obtained culture solution was then filtered off using diatom earth (Fineflow A) as a filtration aid to obtain a filtrate. This filtrate was salted out using an UF module (ACP-2010, Asahi Kasei Corporation) and concentrated. The tannase activity of this concentrated solution was 6.9 unit/ml.

TABLE 4

|  | (w/v) |
|---|---|
| Glucose | 1.0% |
| Gluten meal | 0.5% |
| $NaNO_3$ | 0.5% |
| $KH_2PO_4$ | 0.2% |
| $MgSO_4$ | 0.05% |
| Tannic acid | 2.0% | pH 5.5

Next, the concentrated solution was diluted 2 holds with a 20 mM citric acid buffer solution (pH 3.5), filtrated with a 0.45 μm filter, and then supplied in 5 ml of HiTrap™ Sepharose FF equilibrated with the same buffer solution and diluted with a 20 mM citric acid buffer solution containing 1 M NaCl (pH 3.5) in a linear concentration gradient method to obtain a tannase fraction. This tannase fraction was added and dissolved with ammonium sulfate to have a concentration of 3 M and fractionated with 5 ml of HiTrap™ Phenyl HP equilibrated with a 20 mM citric acid buffer solution containing 3 M ammonium sulfate (pH 5.0). The obtained tannase fraction was salted out using a PD-10 column and concentrated by Amicon (register trade mark) Ultra-15 (MWCO 10,000) to obtain a purified enzyme sample. The obtained purified enzyme was subjected to examination of various properties described below and also subjected to an N-terminal amino acid sequence analysis.

A part of the purified enzyme was subjected to gel filtration HPLC using HiLoad 16/60 Superdex™ 200 pg (Amersham Ltd.) equilibrated with a 20 mM citric acid buffer solution containing 0.15 M NaCl (pH 6.0) and the molecular weight was measured. The molecular weight of the purified enzyme estimated from a diluted site of a molecular weight marker was about 230,000 Da.

When a part of the purified enzyme was subjected to SDS-PAGE, a wide band appeared at 90,000 to 100,000 Da. When a part of the purified enzyme was treated with endoglycosidase H (Roche Co.) and then subjected to SDS-PAGE in the same manner, a sharp band appeared at about 67 KDa.

3. Various Properties of Thermo Stable Tannase (1) Optimum Reaction Temperature

According to the above-mentioned measurement method of a tannase activity, the purified enzyme was reacted at reaction temperatures of 30° C., 35° C., 40° C., 45° C., 50° C., 55° C., 60° C., 65° C., 70° C., 75° C. and 80° C. Each measurement result was shown as a relative activity, assuming a value at a temperature showing the maximum activity as 100% (FIG. 1). The optimum reaction temperature was around 70° C.

(2) Optimum Reaction pH

Figure 2:
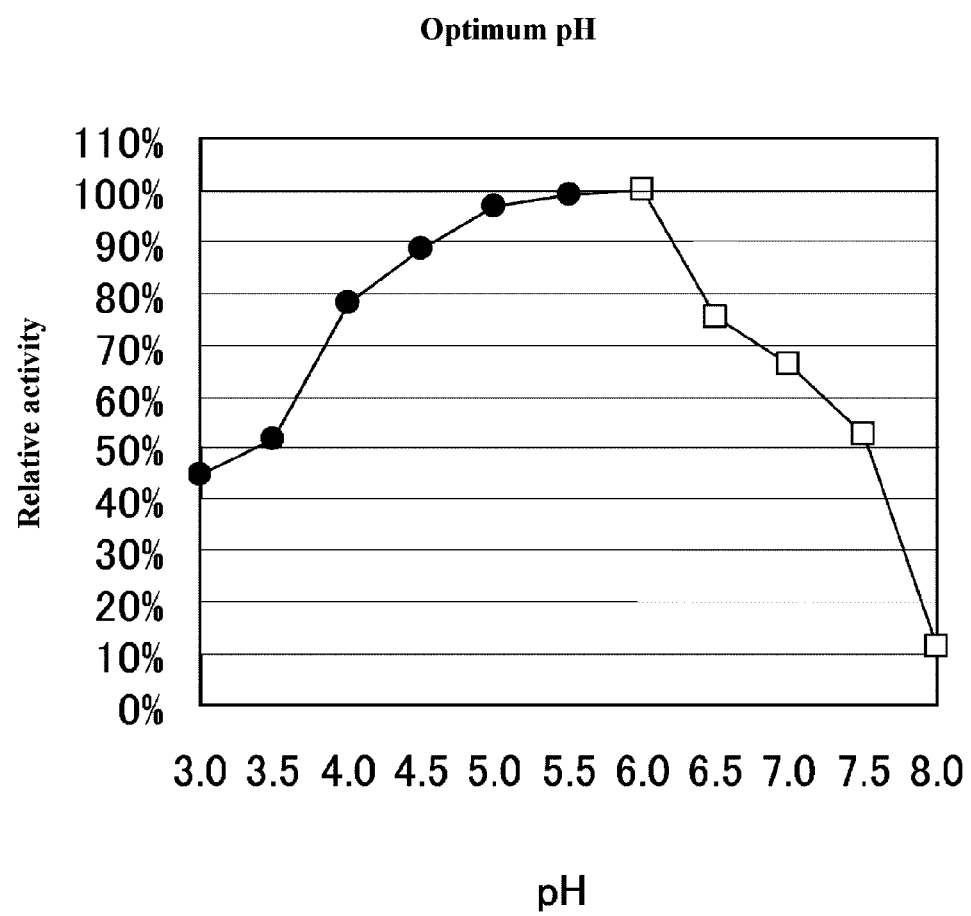
FIG. 2 is a graph showing an optimum pH of tannase derived from *Aspergillus awamori*. •: citric acid buffer at pH3.0, 3.5, 4.0, 4.5, 5.0, 5.5 and 6 □: phosphate buffer at pH6.0, 6.5, 7.0, 7.5 and 8.0

The optimum reaction pH was measured under the reaction condition of 37° C. for 30 minutes in each buffer solution (citric acid buffer solutions at pH 3.0, 3.5, 4.0, 4.5, 5.0, 5.5 and 6.0, and phosphate buffer solutions at pH 6.0, 6.5, 7.0, 7.5 and 8.0) using 1% tannic acid for a substrate. Each measurement result was shown as a relative activity, assuming a value of a pH showing the maximum activity as 100% (FIG. 2). The optimum reaction pH was about 5.5.

(3) Thermostability

Figure 3:
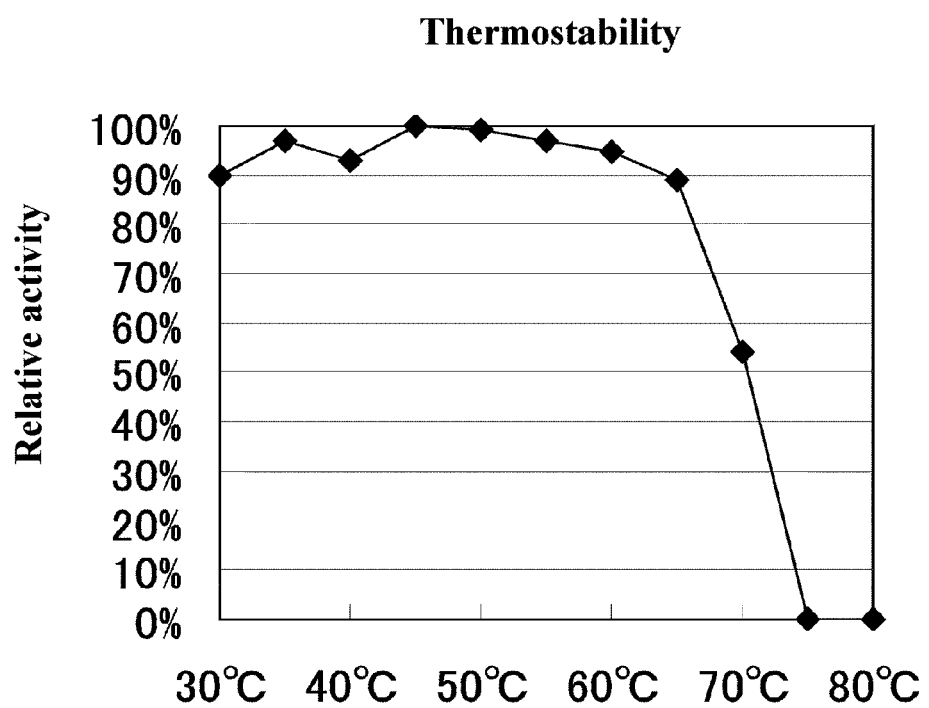
FIG. 3 is a graph showing thermostability of tannase derived from *Aspergillus awamori*.

The purified enzyme was thermally treated for 30 minutes at each temperature of 30° C., 35° C., 40° C., 45° C., 50° C., 55° C., 60° C., 65° C., 70° C., 75° C. and 80° C. in a 50 mM citric acid buffer solution (pH 5.0), and a residual activity was then measured in the above-mentioned measurement method of a tannase activity. Each measurement result was shown as a residual activity, assuming a thermally untreated activity as 100% (FIG. 3). The purified enzyme had 90% or more of a residual activity in the thermal treatment at 65° C. for 30 minutes and was stable until 65° C.

(4) pH Stability

Figure 4:
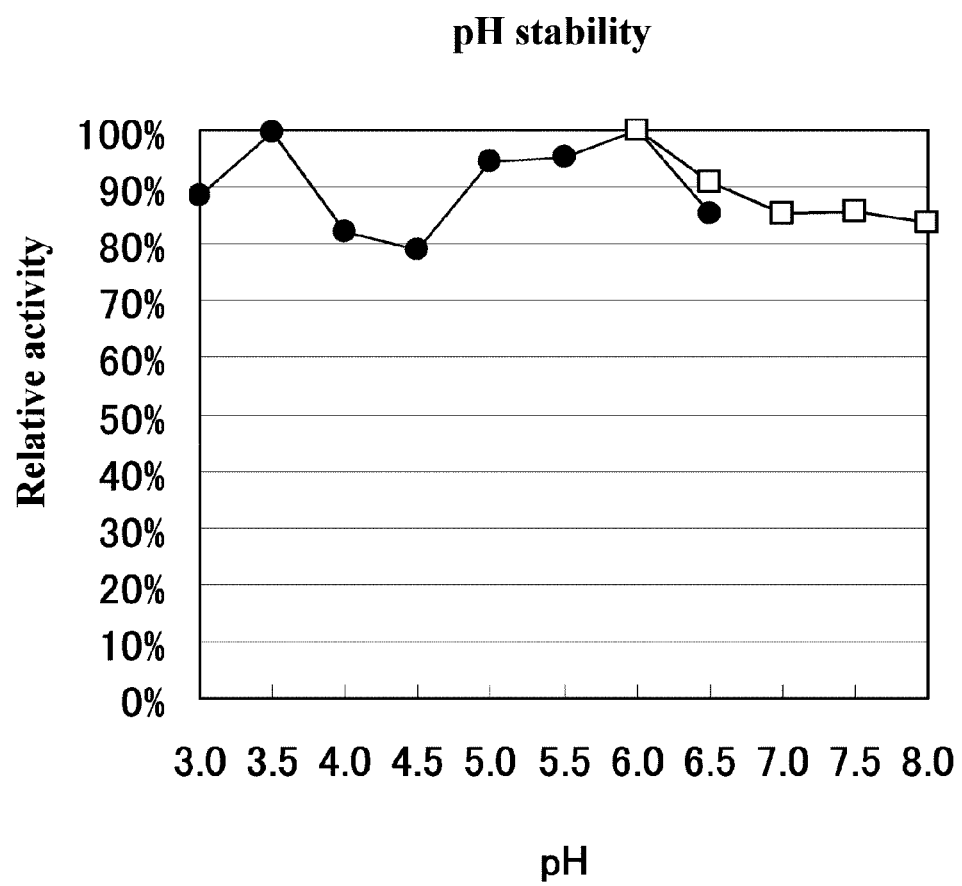
FIG. 4 is a graph showing pH stability of tannase derived from *Aspergillus awamori*. •: citric acid buffer at pH3.0, 3.5, 4.0, 4.5, 5.0, 5.5, 6.0 and 6.5, □: phosphate buffer at pH6.0, 6.5, 7.0, 7.5 and 8.0

The purified enzyme was treated in each buffer solution (citric acid buffer solutions at pH 3.0, 3.5, 4.0, 4.5, 5.0, 5.5 and 6.0, and phosphate buffer solutions at pH 6.0, 6.5, 7.0, 7.5 and 8.0) at 30° C. for 30 minutes and diluted 5 holds with a 0.2 M acetic acid buffer solution (pH 5.0), and an activity was measured in the above-mentioned measurement method of a tannase activity. Each measurement result was shown as a relative activity, assuming a value of a pH showing the maximum activity as 100% (FIG. 4). The stable pH range was from 3 to 8.

(5) Molecular Weight Measurement by SDS-PAGE

SDS-PAGE was carried out in accordance with a method by Laemmli, et al. A molecular weight marker used was a protein molecular weight marker II (TEFCO), and contained, as standard proteins, Myosin, rabbit muscle (205 KDa), galactosidase, E. coli (116 KDa), Phosphorylase b, rabbit-muscle (97.4 KDa), Bovine serum albumin (69 KDa), Glutamic dehydrogenase (55 KDa), Lactic dehydrogenase, porcine muscle (36.5 KDa), Carbonic anhydrase, bovine liver (29 KDa), Trypsin inhibitor, soybean (20.1 KDa), Lysozyme, chicken egg white (14.3 KDa), Aprotinin, bovine lung (6.5 KDa), and Insulin B chain, bovine pancreas (3.5 KDa). Electrophoresis was carried out at 20 mA/gel for about 60 minutes using a gradient gel (Daiichi Pure Chemicals Co., Ltd.) with a gel concentration of 10 to 20% to obtain a molecular weight, and as a result, a wide band appeared at 90,000 to 100,000 Da. When the purified enzyme was treated with endoglycosidase H (Roche Co.) and then subjected to SDS-PAGE in the same manner, the molecular weight thereof was about 67 KDa. Accordingly, it was confirmed that the present enzyme has a sugar chain. Further, this molecular weight corresponded to the size that is calculated from a gene sequence disclosed in the present invention.

(6) Isoelectric Point

When the isoelectric point of the present enzyme was measured by isoelectric electrophoresis using PhastSystem (GE Healthcare Bio-Sciences Ltd.), it was 6.4.

(7) Effect of Metallic Ion and Inhibitor

Tannase in a 50 mM citric acid buffer solution (pH 5.0) was added with each 20 mM metallic ion and EDTA, or 0.4M, 0.8M, 2M and 4M urea, respectively, and treated at 30° C. for 30 minutes, and an activity was then measured in the above-mentioned measurement method of a tannase activity. The result was shown in Table 5. Each measurement result was shown as a relative activity, assuming the case of no addition as 100%. The activity was not inhibited by metallic ions and EDTA. The activity increased by addition of urea.

TABLE 5

| | Relative activity (%) | | (M) | Relative activity (%) |
|---|---|---|---|---|
| $Fe^{3+}$ | 91 | Urea | 0.4 | 108 |
| $Zn^{2+}$ | 82 | | 0.8 | 117 |
| $Cu^{2+}$ | 72 | | 2 | 150 |
| $Mg^{2+}$ | 118 | | 4 | 197 |
| $Ca^{2+}$ | 109 | | | |
| $Mn^{2+}$ | 98 | | | |
| EDTA | 101 | | | |
| No addition | 100 | | | |

(8) Substrate Specificity

Substrate specificities to tannic acid and gallic acid esters (methyl gallate, ethyl gallate, propyl gallate, and isoamyl gallate) were measured in the above-mentioned measurement method of substrate specificity. When a dissolution activity to tannic acid was assumed to be 100%, a dissolution activity of each of the gallic acid esters was 41% for methyl gallate, 30% for ethyl gallate, 29% for propyl gallate, and 27% for isoamyl gallate.

4. Acquisition of Gene Fragment Encoding Tannase derived from *Aspergillus awamori*

(a) Isolation of Chromosome DNA

Genome DNA was prepared from a cell body of *Aspergillus awamori* obtained in 2 by the method of Saito and Miura (Biochim. Biophys. Acta, 72, 619-629, 1963).

(b) Determination of Partial Amino Acid Sequence

The purified sample of tannase obtained in 2 was subjected to an amino acid sequence analysis to determine 7 residues in the N-terminal amino acid sequence (SEQ ID NO: 1). In reference to the revealed sequence, tannase having a corresponding sequence was searched in BLAST. As a result, tannase in which all of the 7 residues were corresponded was only one type of tannase that was *Aspergillus niger* CBS 513.88 hypothetical protein (An04g04430). Other than this tannase, a protein derived from the genus *Aspergillus* in which 7 residues were corresponded was not registered in BLAST.

(c) Preparation of DNA Probe by PCR

Based on the N-terminal amino acid sequence and the sequence of *Aspergillus niger* CBS 513.88 hypothetical protein (An04g04430), 2 types of mixed oligonucleotides were synthesized to form PCR primers (SEQ ID NOs: 2 and 3). These primers and chromosome DNA of *Aspergillus awamori* were used as templates and a PCR reaction was carried out under the following conditions.

<PCR Reaction Solution>
10× PCR reaction buffer solution (Takara Bio Inc.) 5.0
dNTP mixture solution (each 2.5 mM, Takara Bio Inc.) 4.0
25 mM MgCl$_2$ 5 µl
100 µM sense primer 3.0 µl
100 µM antisense primer 3.0 µl
Distilled water 28.5 µl
Chromosome DNA solution (140 µg/ml) 1 µl
LA Taq DNA polymerase (Takara Bio Inc.) 0.5 µl <PCR Reaction Conditions>
Stage 1: Denaturation (94° C., 5 min.) 1 cycle
Stage 2: Denaturation (94° C., 30 sec.) 30 cycles
Annealing (55° C., 30 sec.)
Extension (72° C., 1 min.)

About 0.72 kb of the obtained DNA fragment was cloned to pGEM-Teasy (Promega Co.) and the base sequence thereof was then observed, and as a result, a base sequence encoding the partial amino acid sequence mentioned above was found right after the sense primer. The DNA fragment was used as a DNA probe for cloning a full-length gene.

(d) Preparation of Gene Library

As a result of a Southern hybridization analysis of chromosome DNA of *Aspergillus awamori*, a single band of about 3.6 kb being hybridized with probe DNA in a BamHI+XhoI decomposed product was confirmed. In order to clone this BamHI+XhoI DNA fragment with about 3.6 kb, a gene library was prepared as follows. A BamHI+XhoI treatment was carried out on the chromosome DNA prepared in (a). 10 µg of genome DNA of *Aspergillus awamori*, 5 µl of a 10× K buffer solution, 42 µl of distilled water, and 3 µl of BamHI were mixed and the mixture was treated at 30° C. for 15 hours. The obtained decomposed product was purified by ethanol precipitation, and then mixed with 5 µl of a 10× H buffer solution, 42 µl of distilled water, and 3 µl of XhoI and the mixture was treated at 37° C. for 15 hours. The obtained decomposed product was ligated to a pBluescriptII KS(+) (STRATAGENE Corporation) vector, which was treated with BamHI+XhoI in the same manner, to obtain a gene library.

(e) Screening of Gene Library 0.72 kb of the DNA fragment obtained in (c) was labeled using DIG-High Prime (Roche Co.) The DNA fragment was used as a DNA probe and the gene library obtained in (d) was screened by colony hybridization. A plasmid pBluescriptII-TAN was obtained from the obtained positive colony.

(f) Determination of Base Sequence

The base sequence of a plasmid pBluescriptII-TAN was determined according to a general method. A base sequence (1725 bp) encoding tannase is set forth in SEQ ID NO: 4. An amino acid sequence (574 amino acid residues) encoded by the SEQ ID NO: 4 is set forth in SEQ ID NO: 5. In this amino acid sequence, the N-terminal region amino acid sequence (SEQ ID NO: 1) determined in (b) was found.

5. Expression of Tannase derived from *Aspergillus awamori* in *Aspergillus nidulans*

(a) Construction of Expression Plasmid of Tannase in *Aspergillus nidulans*

Based on the DNA sequence encoding the N-terminal region amino acid sequence and the C-terminal region amino acid sequence, 2 types of oligonucleotides (SEQ ID NOs: 6 and 7) were synthesized to form PCR primers. An Eco22T restriction enzyme recognition site was added to the sense primer, and a KpnI restriction enzyme recognition site was added to the antisense primer. These primers and a plasmid pBluescriptII-TAN having a tannase gene were used as templates and a PCR reaction was carried out under the following conditions.

<PCR Reaction Solution>
10× PCR reaction buffer solution (TOYOBO CO., LTD.) 5.0 µl
dNTP mixture solution(2.5 mM each, TOYOBO CO., LTD.) 5.0 µl
10 µM sense primer 1.5 µl
10 µM antisense primer 1.5 µl
25 mM MgSO$_4$ 2 µl
Distilled water 33 µl
Plasmid pBluescriptII-TAN solution 1.0 µl
KOD-Plus-DNA polymerase (TOYOBO CO., LTD.) 1.0 µl <PCR Reaction Conditions>
Stage 1: Denaturation (94° C., 2 min.) 1 cycle
Stage 2: Denaturation (94° C., 15 sec.) 30 cycles
Annealing (50° C., 30 sec.)
Extension (68° C., 2 min. 30 sec.)

Figure 5:
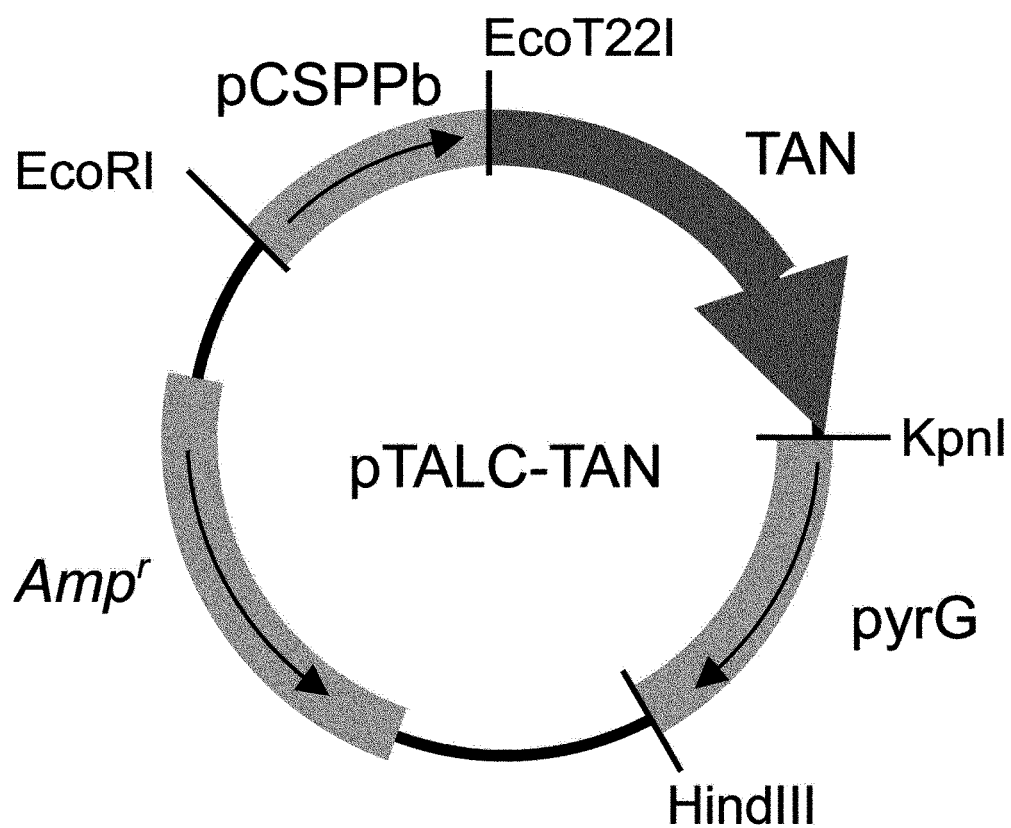
FIG. 5 shows a structure of an expression plasmid pTALC-TAN.

The obtained PCR product was confirmed by electrophoresis and then purified with GENE CLEANE III (15 µl), thereto were added 5 µl of a 10× L buffer solution, 3 µl of KpnI and 41 µL of distilled water and the mixture was treated with an enzyme at 37° C. for 6 hours. The obtained decomposed product was purified by ethanol precipitation, and thereto were added 5 µl of a 10× H buffer solution, 3 µl of EcoT22I and 42 µL of distilled water and the mixture was treated with an enzyme at 37° C. for 15 hours. The obtained decomposed product was confirmed by electrophoresis and purified, and then ligated to an expression vector pTALCPPb (described in Japanese Patent Application Unexamined Publication No. 2003-319786), which has been previously treated with KpnI and EcoT22I, to thus obtain an expression plasmid pTALC-TAN (FIG. 5). pTALCPPb has a pyrG gene and a high expression promoter derived from *Aspergillus oryzae*. Further, it was confirmed that a base sequence encoding tannase in pTALC-TAN was correct.

(b) Expression of Tannase in *Aspergillus nidulans*

An ABPU1 strain (biA1; pyrG89; wA3; argB2; pyroA4: Mol. Gen. Genet., 253:520-528 [1997]) that is an ornithine carbamoyltransferase gene defected strain of *Aspergillus nidulans* was transformed with an expression plasmid pTALC-TAN. A transformation method was carried out by a method using polyethylene glycol and calcium chloride after forming protoplast (Mol. Gen. Genet. 218:99-104, 1989). 7 strains of transformants obtained as uridine non-requiring strains were cultured in the medium of Table 4 mentioned above. *Aspergillus nidulans* ABPU1 transformed with pTAL-CPPb was also cultured as a control in the same manner.

An activity measurement was carried out on the obtained samples according to the above-mentioned measurement method of a tannase activity, and the results are shown in Table 6 below. Tannase activities were observed in 6 strains out of the 7 strains.

TABLE 6

|  | U/mL |
|---|---|
| *A. nidulans* ABPU1 | ND |
| No. 1 | ND |
| No. 2 | 4.92 |
| No. 3 | 3.97 |
| No. 4 | 0.41 |
| No. 5 | 0.17 |
| No. 6 | 0.73 |
| No. 7 | 2.53 |

INDUSTRIAL APPLICABILITY

The tannase of the present invention has high thermostability such as 90% or more of a residual activity after a treatment at 65° C. for 30 minutes and is preferable for applications in which a reaction at a high temperature is desired. Use of the tannase of the invention makes it possible to carry out an enzyme reaction at a high temperature where a fear of contamination is less. Therefore, the tannase of the invention is particularly useful for applications in food processing.

The invention is not construed by description of the embodiments and examples of the invention described above at all. Various modified embodiments are also included in the invention within the range that a person skilled in the art can easily conceived of, without deviating the description of the scope of patent claims.

Contents of treatises, unexamined patent publications, and examined patent publications specified in this specification are all incorporated herewith by their references.

The invention claimed is:

1. An isolated tannase having the amino acid sequence set forth in SEQ ID NO: 5 or an amino acid sequence that is 90% or more identical to the amino acid sequence set forth in SEQ ID NO: 5 and having the following chemoenzymatic properties:
   (1) activity: to act on a depside bond to thereby cause hydrolysis;
   (2) molecular weight: about 230,000 Da (as measured by gel filtration); and
   (3) thermostability: stable at a temperature up to 65° C. (pH 5.0, 30 min.).

2. The isolated tannase according to claim 1, further having the following chemoenzymatic properties:
   (4) optimum temperature: about 70° C.;
   (5) optimum pH: about 5.5;
   (6) pH stability: stable within the range from pH 3 to 8 (30° C., 30 min.); and
   (7) substrate specificity: preferably act on tannic acid, and act on gallic acid esters.

3. The isolated tannase according to claim 1, obtained from *Aspergillus awamori*.

4. The isolated tannase of claim 1, wherein the amino acid sequence is 95% or more identical to the amino acid sequence set forth in SEQ ID NO: 5.

5. The isolated tannase according to claim 4, wherein the amino acid sequence is 99% or more identical to the amino acid sequence set forth in SEQ ID NO: 5.

6. An enzyme preparation comprising the isolated tannase according to claim 1 as an active ingredient.

7. A hydrolysis process, wherein tannase according to claim 1 acts on tannin or a tannin-containing composition.

8. The isolated tannase according to claim 5, wherein the amino acid sequence is identical to the amino acid sequence set forth in SEQ ID NO: 5.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Aspergillus awamorii
<220> FEATURE:
<221> NAME/KEY: MISC_FEATURE
<222> LOCATION: (1)..(1)
<223> OTHER INFORMATION: Xaa may be G
<220> FEATURE:
<221> NAME/KEY: MISC_FEATURE
<222> LOCATION: (4)..(4)
<223> OTHER INFORMATION: Xaa may be A or S

<400> SEQUENCE: 1

Xaa Thr Pro Xaa Thr Leu Ala Glu Leu
1               5

<210> SEQ ID NO 2
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 2
```

```
acnccntcnc anttrgcnga                                                    20

<210> SEQ ID NO 3
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 3
ytcrcanggn ggnggrtart a                                                  21

<210> SEQ ID NO 4
<211> LENGTH: 1725
<212> TYPE: DNA
<213> ORGANISM: Aspergillus awamorii

<400> SEQUENCE: 4
atgcgctcac ccgcttgggc ttccatagcc atcacagcct tgcggcatt ggcaaatgct         60 ggaactcctt ctacgttggc ggagctttgc actgattcca ttgtgaaggc agctctacca        120
ccctctgaat tcatcaaagg cataacaatt gactcggact ctgtgacgac cgaagtcgta        180
acgaacagca gtttctccag cgaattttac ccaagcgcca cgattgacta ttgcaacgtc        240
acatttgcct actcccacga tggcattgac ggtgaccaag tccttttgga aatctggctc        300
cccgcaccaa caaatttcaa aaaccgctgg ctctccactg gcggaggtgg ttatgccatc        360
aattccggag accaatcgtt gccaggtggt gtcatgtatg gggccgcgtc aggtatgaca        420
gatggcggtt ttgggggatt ctcaaacaat gcggacacgg ctatgctgtt ggcgaatggc        480
acactcaact acgagacgct ttacatgttt gcatacaagg cgcatcggga gcttagcttg        540
cttggaaagg ccctgacccg caatgtttac gggatgagcg acagcgataa gctgtatgcg        600
tattatcaag gctgctctga aggaggccgc gaaggttgga gtcaagtgca gcgattcggc        660
gatgaatggg atggagccat cattggtgct ccagcattcc gctggtcctt ccaacagact        720
caacatctct attccaacat cgtcgagaag acactggatt actacccacc cccctgtgag        780
ctggacaaga tcgtcaacga gaccatcgct gcctgtgatg ccatggacgg aaaggtagat        840
tgggtggttg cacggaccga tctctgcttg ctcgactttg acattagtac aatcgagggt        900 aagcccctact catgcgctgc atccaggggc accctgcac agaatggcac ggtctccgcc        960
aagggtatcg aagtcgcgaa aaccatcatc aatggattgc atgactccca aggcgccgtt       1020
gtctactttt cctaccagcc tacagccgcc ttcgatgatg ccgagacgca gtacaactcc       1080
acaacaggcc aatggggggct cgatatcgat cagcttggag gcgaatatat tgctctcttg       1140
gtagacaaga atggcactac actggacagc ctggatggaa ttacctatga cacgcttaag       1200
gactggatga tctccggctt gcaggaatac tacagcacct tgcagaccac atggccggac       1260
ctcacgccct tccacaatgc tggaggtaaa gtcatccatt ccatggtgga tgccgacttc       1320
agtattccaa ccgccgcatc catccgctat tgggaatcag tccgcagcat tatgtacccc       1380
```

```
aataaggact ataactccag tgctgaggcg ctcaatgagt ggtatcgcct gtacactgtc    1440
ccaggagcgg gtcattgtgc gaccaacgat gctatgccca acggcccctt cccacagacg    1500
aacatggctg tgatgatcga ctgggtggag aacggagtag tgcctacaac gctgaatgcg    1560
accgtgctcc agggagagaa tgaaggacag aaccagcagc tctgtgcttg gccactgcga    1620
cccttgtgga ccaacaatgg caccaccatg gagtgcgtgt ataaccgcg ttcaattgac    1680 agctggcatt atgacttgga tgcggttccc atgcctgtgt actag                    1725
```

<210> SEQ ID NO 5
<211> LENGTH: 574
<212> TYPE: PRT
<213> ORGANISM: Aspergillus awamorii

<400> SEQUENCE: 5

```
Met Arg Ser Pro Ala Trp Ala Ser Ile Ala Ile Thr Ala Phe Ala Ala
1               5                   10                  15

Leu Ala Asn Ala Gly Thr Pro Ser Thr Leu Ala Glu Leu Cys Thr Asp
            20                  25                  30

Ser Ile Val Lys Ala Ala Leu Pro Pro Ser Glu Phe Ile Lys Gly Ile
        35                  40                  45

Thr Ile Asp Ser Asp Ser Val Thr Thr Glu Val Val Thr Asn Ser Ser
    50                  55                  60

Phe Ser Ser Glu Phe Tyr Pro Ser Ala Thr Ile Asp Tyr Cys Asn Val
65                  70                  75                  80

Thr Phe Ala Tyr Ser His Asp Gly Ile Asp Gly Asp Gln Val Leu Leu
                85                  90                  95

Glu Ile Trp Leu Pro Ala Pro Thr Asn Phe Lys Asn Arg Trp Leu Ser
            100                 105                 110

Thr Gly Gly Gly Gly Tyr Ala Ile Asn Ser Gly Asp Gln Ser Leu Pro
        115                 120                 125

Gly Gly Val Met Tyr Gly Ala Ala Ser Gly Met Thr Asp Gly Gly Phe
    130                 135                 140

Gly Gly Phe Ser Asn Asn Ala Asp Thr Ala Met Leu Leu Ala Asn Gly
145                 150                 155                 160

Thr Leu Asn Tyr Glu Thr Leu Tyr Met Phe Ala Tyr Lys Ala His Arg
                165                 170                 175

Glu Leu Ser Leu Leu Gly Lys Ala Leu Thr Arg Asn Val Tyr Gly Met
            180                 185                 190

Ser Asp Ser Asp Lys Leu Tyr Ala Tyr Tyr Gln Gly Cys Ser Glu Gly
        195                 200                 205

Gly Arg Glu Gly Trp Ser Gln Val Gln Arg Phe Gly Asp Glu Trp Asp
    210                 215                 220

Gly Ala Ile Ile Gly Ala Pro Ala Phe Arg Trp Ser Phe Gln Gln Thr
225                 230                 235                 240

Gln His Leu Tyr Ser Asn Ile Val Glu Lys Thr Leu Asp Tyr Tyr Pro
                245                 250                 255

Pro Pro Cys Glu Leu Asp Lys Ile Val Asn Glu Thr Ile Ala Ala Cys
            260                 265                 270

Asp Ala Met Asp Gly Lys Val Asp Trp Val Val Ala Arg Thr Asp Leu
        275                 280                 285

Cys Leu Leu Asp Phe Asp Ile Ser Thr Ile Glu Gly Lys Pro Tyr Ser
    290                 295                 300

Cys Ala Ala Ser Arg Gly Thr Pro Ala Gln Asn Gly Thr Val Ser Ala
305                 310                 315                 320
```

Lys Gly Ile Glu Val Ala Lys Thr Ile Ile Asn Gly Leu His Asp Ser
            325                 330                 335

Gln Gly Arg Arg Val Tyr Phe Ser Tyr Gln Pro Thr Ala Ala Phe Asp
            340                 345                 350

Asp Ala Glu Thr Gln Tyr Asn Ser Thr Thr Gly Gln Trp Gly Leu Asp
            355                 360                 365

Ile Asp Gln Leu Gly Gly Glu Tyr Ile Ala Leu Leu Val Asp Lys Asn
            370                 375                 380

Gly Thr Thr Leu Asp Ser Leu Asp Gly Ile Thr Tyr Asp Thr Leu Lys
385                 390                 395                 400

Asp Trp Met Ile Ser Gly Leu Gln Glu Tyr Tyr Ser Thr Leu Gln Thr
                405                 410                 415

Thr Trp Pro Asp Leu Thr Pro Phe His Asn Ala Gly Gly Lys Val Ile
                420                 425                 430

His Phe His Gly Asp Ala Asp Phe Ser Ile Pro Thr Ala Ala Ser Ile
                435                 440                 445

Arg Tyr Trp Glu Ser Val Arg Ser Ile Met Tyr Pro Asn Lys Asp Tyr
            450                 455                 460

Asn Ser Ser Ala Glu Ala Leu Asn Glu Trp Tyr Arg Leu Tyr Thr Val
465                 470                 475                 480

Pro Gly Ala Gly His Cys Ala Thr Asn Asp Ala Met Pro Asn Gly Pro
                485                 490                 495

Phe Pro Gln Thr Asn Met Ala Val Met Ile Asp Trp Val Glu Asn Gly
                500                 505                 510

Val Val Pro Thr Thr Leu Asn Ala Thr Val Leu Gln Gly Glu Asn Glu
            515                 520                 525

Gly Gln Asn Gln Gln Leu Cys Ala Trp Pro Leu Arg Pro Leu Trp Thr
            530                 535                 540

Asn Asn Gly Thr Thr Met Glu Cys Val Tyr Asn Gln Arg Ser Ile Asp
545                 550                 555                 560

Ser Trp His Tyr Asp Leu Asp Ala Val Pro Met Pro Val Tyr
                565                 570

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
aggatgcatt cacccgcttg g                                       21

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
ccgggtaccg tgatctagca tgagtc                                  26